(12) United States Patent
Verser (10) Patent No.: US 8,252,567 B2
(45) Date of Patent: Aug. 28, 2012

(54) METHOD FOR THE INDIRECT PRODUCTION OF BUTANOL AND HEXANOL

(75) Inventor: Dan W. Verser, Menlo Park, CA (US)

(73) Assignee: ZeaChem, Inc., Menlo Park, CA (US)

( * ) Notice: Subject to any disclaimer, the term of this patent is extended or adjusted under 35 U.S.C. 154(b) by 557 days.

(21) Appl. No.: 12/368,040

(22) Filed: Feb. 9, 2009

(65) Prior Publication Data
US 2009/0203098 A1   Aug. 13, 2009

Related U.S. Application Data

(60) Provisional application No. 61/026,910, filed on Feb. 7, 2008.

(51) Int. Cl.
*C12P 7/14* (2006.01)
(52) U.S. Cl. ........................ 435/162; 435/163
(58) Field of Classification Search .................. 435/160, 435/162, 170, 163
See application file for complete search history.

(56) References Cited

U.S. PATENT DOCUMENTS

| | | |
|---|---|---|
| 1,421,605 A | 7/1922 | Steffens |
| 2,079,414 A | 5/1937 | Lazier |
| 2,565,487 A | 8/1951 | Filachione et al. |
| 2,782,243 A | 2/1957 | Hess et al. |
| 3,769,329 A | 10/1973 | Paulik et al. |
| 4,055,590 A | 10/1977 | Gruber et al. |
| 4,100,189 A | 7/1978 | Mercier |
| 4,113,662 A | 9/1978 | Wall |
| 4,275,234 A | 6/1981 | Baniel et al. |
| 4,282,323 A | 8/1981 | Yates |
| 4,353,784 A | 10/1982 | Koga et al. |
| 4,370,507 A | 1/1983 | Hargis et al. |
| 4,371,619 A | 2/1983 | Schwartz et al. |
| 4,405,717 A | 9/1983 | Urbas |
| 4,421,939 A | 12/1983 | Kiff et al. |
| 4,431,838 A | 2/1984 | Feldman et al. |
| 4,444,881 A | 4/1984 | Urbas |
| 4,454,358 A | 6/1984 | Kummer et al. |
| 4,497,967 A | 2/1985 | Wan |
| 4,568,644 A | 2/1986 | Wang et al. |
| 4,649,112 A | 3/1987 | Datta et al. |
| 4,830,963 A | 5/1989 | Brumm et al. |
| 4,935,360 A | 6/1990 | Klemps et al. |
| 4,939,294 A | 7/1990 | Agreda et al. |
| 5,071,754 A | 12/1991 | Walkup et al. |
| 5,137,818 A | 8/1992 | Harder et al. |
| 5,210,296 A | 5/1993 | Cockrem et al. |
| 5,412,126 A | 5/1995 | King et al. |
| 5,424,202 A | 6/1995 | Ingram et al. |
| 5,563,069 A | 10/1996 | Yang |
| 5,591,877 A | 1/1997 | Obermeier et al. |
| 5,599,976 A | 2/1997 | Scates et al. |
| 5,620,877 A | 4/1997 | Farone et al. |
| 5,693,296 A | 12/1997 | Holtzapple et al. |
| 5,723,639 A | 3/1998 | Datta et al. |
| 5,753,474 A * | 5/1998 | Ramey .......................... 435/136 |
| 5,766,439 A | 6/1998 | Eyal et al. |
| 5,773,653 A | 6/1998 | Baniel |
| 5,780,276 A | 7/1998 | Baniel |
| 5,865,898 A | 2/1999 | Holtzapple et al. |
| 5,874,263 A | 2/1999 | Holtzapple et al. |
| 5,986,133 A | 11/1999 | Holtzapple et al. |
| 6,043,392 A | 3/2000 | Holtzapple et al. |
| 6,136,577 A | 10/2000 | Gaddy |
| 6,160,173 A | 12/2000 | Eyal et al. |
| 6,262,313 B1 | 7/2001 | Holtzapple et al. |
| 6,284,904 B1 | 9/2001 | Ponnampalam |
| 6,368,819 B1 | 4/2002 | Gaddy et al. |
| 6,395,926 B1 | 5/2002 | Holtzapple et al. |
| 6,478,965 B1 | 11/2002 | Holtzapple et al. |
| 6,509,180 B1 | 1/2003 | Verser et al. |
| 6,703,227 B2 | 3/2004 | Jakel et al. |
| 6,740,508 B2 | 5/2004 | Ulrich et al. |
| 6,926,810 B2 | 8/2005 | Cockrem et al. |
| 6,927,048 B2 | 8/2005 | Verser et al. |
| 7,074,603 B2 | 7/2006 | Verser et al. |
| 7,309,602 B2 * | 12/2007 | David ........................ 435/254.2 |
| 7,351,559 B2 | 4/2008 | Verser et al. |
| 7,507,562 B2 | 3/2009 | Verser et al. |
| 7,601,865 B2 | 10/2009 | Verser et al. |
| 7,682,812 B2 | 3/2010 | Verser et al. |

(Continued)

FOREIGN PATENT DOCUMENTS
GB          933714         8/1963
(Continued)

OTHER PUBLICATIONS

International Preliminary Report on Patentability for International (PCT) Patent Application No. PCT/US09/33561, mailed Aug. 19, 2010.

(Continued)

*Primary Examiner* — Ralph Gitomer
(74) *Attorney, Agent, or Firm* — Sheridan Ross P.C.

(57) ABSTRACT

A process for the conversion of carbohydrates from any of a number of sources into butanol and hexanol for fuel or chemical use is disclosed. The process includes conducting a homoacetogenic fermentation to produce an acetic acid intermediate which is chemically converted to ethanol. The ethanol and a remaining portion of the acetic acid intermediate are used as a substrate in an acidogenic fermentation to produce butyric and caproic acid intermediates which are then chemically converted to butanol and hexanol.

36 Claims, 2 Drawing Sheets

U.S. PATENT DOCUMENTS

| | | | |
|---|---|---|---|
| 2003/0077771 A1* | 4/2003 | Verser et al. ............... | 435/161 |
| 2005/0112739 A1 | 5/2005 | Golubkov | |
| 2006/0024801 A1 | 2/2006 | Holtzapple et al. | |
| 2006/0222585 A1 | 10/2006 | Verser et al. | |
| 2007/0014895 A1 | 1/2007 | Holtzapple et al. | |
| 2008/0102502 A1 | 5/2008 | Foody et al. | |
| 2008/0176301 A1 | 7/2008 | Granda et al. | |
| 2008/0193989 A1 | 8/2008 | Verser et al. | |
| 2008/0248540 A1* | 10/2008 | Yang ........................... | 435/160 |
| 2008/0280338 A1 | 11/2008 | Hall et al. | |
| 2009/0081749 A1 | 3/2009 | Verser et al. | |
| 2009/0281354 A1 | 11/2009 | Mariansky et al. | |
| 2010/0120104 A1* | 5/2010 | Reed ........................... | 435/140 |

FOREIGN PATENT DOCUMENTS

| | | |
|---|---|---|
| JP | S57-140732 | 8/1982 |
| JP | S59-29633 | 2/1984 |
| JP | S61-007222 | 1/1986 |
| JP | S62-171689 | 7/1987 |
| JP | 11-503514 | 3/1999 |
| WO | WO 82/03854 | 11/1982 |
| WO | WO 83/03409 | 10/1983 |
| WO | WO 93/00440 | 1/1993 |
| WO | WO 99/00352 | 1/1999 |
| WO | WO 99/00512 | 1/1999 |
| WO | WO 00/53791 | 9/2000 |
| WO | WO 2006/007406 | 1/2006 |
| WO | WO 2007/009085 | 1/2007 |
| WO | WO 2008/070561 | 6/2008 |
| WO | WO 2009/018149 | 2/2009 |

OTHER PUBLICATIONS

Jones et al., "Acetone-Butanol Fermentation Revisited," Microbial Reviews, Dec. 1986, vol. 50(4), pp. 484-524.
Xin et al., "Recovery of acetic acid from waste water," Chemical Engineering (China), Oct. 25, 1996, vol. 24(5), pp. 41-44 (including translated abstract).
U.S. Appl. No. 12/511,526, filed Jul. 29, 2009, Verser et al.
U.S. Appl. No. 12/548,312, filed Aug. 26, 2009, Verser et al.
U.S. Appl. No. 12/693,533, filed Jan. 26, 2010, Verser et al.
Agreda et al., Chem. Eng. Prog., "High Purity Methyl Acetate by Reactive Distillation", pp. 40-46, Feb. 1990.
Balasubramanian, N., Kim, J.S., Lee, Y.Y., "Fermentation of Xylose into Acetic Acid by *Clostridium thermoaceticum*", Appl Biochem and Biotech, vol. 91-93, p. 367-376, 2001.
Borden, J.R., Lee, Y.Y., Yoon, H.H., "Simultaneous Saccharification and Fermentation of Cellulosic Biomass to Acetic Acid", Appl Biochem and Biotech, vol. 84-86, p. 963-970, 2000.
Brownell, J., Nakas, J., "Bioconversion of Acid-Hydrolyzed Poplar Hemicellulose to Acetic Acid by *Clostridium thermoaceticum*", J. Ind. Microbiol, vol. 7, p. 1-6, 1991.
Busche et al., Biotechnol. Bioeng. Symp., "Recovery of Acetic Acid From Dilute Acetate Solution", No. 12, pp. 249-262 (1982).
Busche, Robert M., Recovering Chemical Products from Dilute Fermentation Broths, Biotechnology and Bioengineering Symp. No. 13, 597-615 (1983).
Buschhom, H., et al., "Production and utilization of ethanol by the homoacetogen *Acetobacterium woodii*," Appl. Environ. Microbiol. 55, 1835-1840 (1989).
Drake, "Acetogenesis, Acetogenic Bacteria, and the Acetyl-CoA 'Wood/Ljungdahl' Pathway: Past and Current Perspectives", Acetogenesis, 1994, Chapter 1, pp. 3-60, Chapman and Hall, Inc., New York, NY.
Drake, Acetogenesis, Figure 12.2, 1994, p. 343, Chapman Hall, New York.
Drake, et al, "Old Acetogens, New Light" Ann. NY Acad. Sci. 1125: 100-128 (2008).
Eggeman et al. "Recovery of Organic Acids from Fermentation Broths", Mar. 1, 2005, Applied Biochemistry and Biotechnology, vol. 122, pp. 605-618.
Eggeman Tim et al: "The importance of utility systems in today's biorefineries and a vision for tomorrow" Applied Biochemistry and Biotechnology, vol. 130, No. 1-3, Mar. 2006, pp. 361-381, XP002499935 ISSN: 0273-2289.

Filachione et al., Preparation of Esters by Reaction of Ammonium Salts with Alcohols, 5265-5267 (Nov. 1951) [Presented in part at the 116th A.C.S. Meeting held in Atlantic City, N.J., Sep. 1949, and also at the Miniature meeting of the Philadelphia Section of the American Chemical Society held in Philadelphia, PA., in Jan. 1949.].
Husson et al., Regeneration of Lactic and Succinic Acid-Laden Basic Sorbents by Leaching with a Volatile Base in an Organic Solvent, Ind. Eng. Chem. Res. 37:2996-3005 (1998).
Jones et al. "Acetone-Butanol Fermentation Revisited", Microbial Reviews, Dec. 2006; 50(4); 484-524.
Luedeking et al., J. Biochem. Microbiol. Tech. Eng., "A Kinetic Study of the Lactic Acid Fermentation; Batch Process at Controlled PH", Robert Luedeking & Edgar L. Piret, vol. 1, No. 1, pp. 393-412, 1959.
McCoy "Biomass Ethanol Inches Forward", C&EN, Dec. 7, 1998, p. 29-32.
Miller, Richard W. et al: "Extraction of Lactic Acid from a Calcium Lactate Solution Using Amine-Containing Solvents and Carbon Dioxide Gas. 1. Experimental Procedures" Industrial & Engineering Chemistry Research, 35(4), 1156-62, 1996.
Othmer, "Acetic Acid Recovery Methods", Chemical Engineering Progress, Jul. 1958, pp. 48-59, vol. 54, No. 7.
Parekh et al., Acetate Production from Glucose by *Clostridium thermoaceticum*, Process Biochemistry International, 117-121 (Aug. 1990).
Pöpken, et al., "Reaction Kinetics and Chemical Equilibrium of Homogeneously and Heterogeneously Catalyzed Acetic Acid Esterification with Methanol and Methyl Acetate Hydrolysis", Industrial and Engineering Chemistry Research, Jun. 17, 2000, pp. 2601-2611, vol. 39, No. 7.
Richert et al., "Thermophilic Fermentation to Make Ethanol from Carbohydrate Byproducts", Genetic Engineering News, Oct. 1, 1998, 1 page.
Ricker et al., Solvent Extraction With Amines for Recovery of Acetic Acid From Dilute Aqueous Industrial Streams, J. Separ. Proc. Technol., 1(2):23-30 (1980).
Ricker, et al., "Solvent Properties of Organic Bases for Extraction of Acetic Acid from Water", Journal of Separation Process Technology, 1979, pp. 36-41, vol. 1, No. 1.
Saha, et al., "Recovery of dilute acetic acid through esterification in a reactive distillation column", Catalysis Today, 2000, pp. 147-157, vol. 60.
Savage, M.D., Drake, H.L., "Adaptation of the Acetogen *Clostridium thermoautotropicum* to Minimal Medium", Journal of Bacteriology, vol. 165, No. 1, p. 315-318, 1986.
Schoberth et al., "Considerations on the Energy Metabolism of *Clostridium kluyveri*" Arch. Mikrobiol. 65, 318-328 (1969).
Seedorf et al. "The genome of *Clostridium kluyveri*, a strict anaerobe with unique metabolic features", PNAS, Feb. 12, 2008, vol. 105, No. 6, pp. 2128-2133.
Stanier et al, The Microbial World, Prentice Hall, 1976, pp. 652-661.
Talabardon et al., "Anaerobic thermophilic fermentation fro acetic acid production from milk permeate", Journal of Biotechnology, vol. 76, Issue 1, Jan. 7, 2000, pp. 83-92.
Tamada et al., Extraction of Carboxylic Acids with Amine Extractants. 3. Effect of Temperature, Water Coextraction, and Process Considerations, Ind. Eng. Chem. Res. 29:1333-1338 (1990).
Tang et al., Appl. Microbiol. Biotechnol., "Acetic Acid Production From Whey Lactose by the Co-Culture of Sterpococcus Lactis and *Clostridium formicoaceticum*", 28:138-143 (1988).
Thauer et al., "The Energy Metabolism of *Clostridiium kluyveri*" European J. Biochem., 4 (1968) pp. 173-180.
Wang et al., Biochem. Eng. Renewable Sources, "A Novel Route to the Production of Acetic Acid by Fermentation", No. 181, vol. 74, pp. 105-110 (1978).
Wang, et al., "Elucidation of Growth Inhibition and Acetic Acidm Production by *Clostridium thermaoaceticum*", Applied and Environmental Microbiology, Feb. 1984, pp. 294-298 vol. 47, No. 2.
Wardell et al., Solvent Equilibria for Extraction of Carboxylic Acids from Water, Journal of Chemical and Engineering Data, 23(2):144-148 (1978).

Witjitra, K., Shah, M.M., Cheryan, M., "Effect of Nutrient Sources on Growth and Acetate Production by *Clostridium thermoaceticum*", Enzyme and Microbial Technology, vol. 19, p. 322-327, 1996.

Xin et al. "Recovery of acetic acid from waste water", Chemical Engineering (China), vol. 24, No. 5, pp. 41-44 (including translated abstract), Oct. 1996.

Zeikus et al., "Thermophilic Ethanol Fermentations", Basic Life Sci, 1981, vol. 18, p. 441-61 (Abstract only).

Zhicai et al., Esterification—Distillation of Butanol and Acetic Acid, Chemical Engineering Science, 53(11):2081-2088 (1998).

International Search Report for International (PCT) Patent Application No. PCT/US09/33561, mailed Apr. 2, 2009.

Written Opinion for International (PCT) Patent Application No. PCT/US09/33561, mailed Apr. 2, 2009.

* cited by examiner

METHOD FOR THE INDIRECT PRODUCTION OF BUTANOL AND HEXANOL

CROSS REFERENCE TO RELATED APPLICATION

This application claims priority under 35 U.S.C. §119(e) to U.S. Provisional Patent Application Ser. No. 61/026,910 entitled "INDIRECT PRODUCTION OF BUTANOL AND HEXANOL" filed Feb. 7, 2008, which is incorporated herein in its entirety by this reference.

FIELD OF THE INVENTION

This invention relates to a process for the conversion of carbohydrates from any of a number of sources into butanol and hexanol for fuel or chemical use. The invention uses a combination of homoacetogenic fermentation and acidogenic fermentation to greatly increase the yield of butanol and hexanol from carbohydrates.

BACKGROUND OF THE INVENTION

The acetone-butanol-ethanol fermentation (ABE) has been known and practiced industrially for nearly 100 years. The biology, history and technology are reviewed in detail by Acetone-Butanol Fermentation Revisited, Microbial Reviews, Dec. 1986; 50(4); 484-524. The yield of total solvents, A+B+E, from carbohydrates are reported as about 32% w/w. There are two phases in the fermentation in which first acids are produced and subsequently solvents are produced from the acids. However not all of the acids, mainly acetic acid and butyric acid, are converted to solvents, so the final fermentation broth contains a number of co-products which need to be recovered or treated. Major co-products are also $H_2$ and $CO_2$. All of the biochemical pathways have been studied. Many attempts have been made to improve the yield and process economics of the process. A number of processes have been proposed to use the carbohydrates from biomass as the feedstock. However the main limitation is the low overall yield of the target solvents and thus poor economics which has caused all industrial production to be ended. It is a very mature technology.

Recently it has been proposed to use a hybrid process in which butyric acid is produced and then subsequently converted to butanol in a separate hydrogenation step. The advantage is that a fermentation organism can be chosen that produces butyric acid plus gaseous co-products such as *Clostridium tyrobutylicum* as proposed in US Patent Publication 2008/0248540. However this organism and most butyric acid bacteria also produce $CO_2$ so that the carbon yield is low. The yield reported in the proposed process is 41% w/w on a theoretical basis.

While the ability to produce butanol and other solvents has been proven industrially and improved through further research, it would be desirable to find a process with higher yield which had better economics and could compete on an industrial basis.

SUMMARY OF THE INVENTION

One method of the present invention is a method to produce butanol and hexanol. The method includes conducting a homoacetogenic fermentation in a medium that includes a carbohydrate source to produce acetate, acetic acid or mixtures thereof. A portion of the acetate, acetic acid or mixtures is chemically converted to ethanol. An acidogenic fermentation is conducted in a medium that comprises the ethanol and a portion of the acetate, acetic acid or mixtures thereof to produce butyrate, butyric acid, caproate, caproic acid or mixtures thereof. The method further includes chemically converting the butyrate, butyric acid, caproate, caproic acid or mixtures thereof to butanol and hexanol.

In various embodiments of this method, at least about 70%, at least about 80% or at least about 90%, of carbon in the carbohydrate source is converted into butanol and hexanol. In other embodiments, essentially none of the carbon in the carbohydrate source is evolved as carbon dioxide. In other embodiments, when the carbohydrate source is a material comprising carbon-containing compounds with less than about 75% by weight of the carbon-containing compounds being carbohydrate substances, the chemical energy efficiency of the method can be at least about 50%, at least about 60%, or at least about 70%. In other embodiments, when the carbohydrate source is a material that includes carbon-containing compounds with less than about 75% by weight of the carbon-containing compounds being carbohydrate substances, the yield of butanol and hexanol can be at least about 100 gal/BDT of the carbohydrate source, at least about 120 gal/BDT of the carbohydrate source, or at least about 140 gal/BDT of the carbohydrate source.

In another embodiment of this method, the step of chemically converting a portion of the acetate, acetic acid or mixtures thereof to ethanol can include acidifying the homoacetogenic fermentation medium to convert acetate to acetic acid, esterifying the acetic acid, and reducing the acetic acid ester to form ethanol. In this embodiment, the step of acidifying can include introducing carbon dioxide, or an acid with a pKa lower than acetic acid, to the fermentation medium comprising a salt of acetic acid. Alternatively, in this embodiment, the step of acidifying can comprise introducing an amine with carbon dioxide to the fermentation medium to form an acetic acid/amine complex. This embodiment can also include contacting the acid/amine complex with a water immiscible solvent to form an ester of the water immiscible solvent and the acetic acid.

The step of chemically converting butyrate, butyric acid, caproate, caproic acid or mixtures thereof to butanol and hexanol can include acidifying the acidogenic fermentation medium to convert butyrate and caproate to butyric acid and caproic acid, esterifying the butyric acid and caproic acid, and reducing the butyric acid and caproic acid esters to form butanol and ethanol. In this embodiment, the step of acidifying can include introducing carbon dioxide, or an acid with a pKa lower than butyric acid and caproic acid, to the fermentation medium comprising a salt of butyric acid and caproic acid. Alternatively, the step of acidifying can include introducing an amine with carbon dioxide to the fermentation medium to form butyric acid/amine and caproic acid/amine complexes. This embodiment can also include contacting the acid/amine complexes with a water immiscible solvent to form an ester of the water immiscible solvent and the butyric acid and an ester of the water immiscible solvent and the caproic acid.

In any of the embodiments, the step of reducing can be conducted with a reductant that is produced by thermochemical processing of a portion of a carbon-containing material. In such embodiments, the thermochemical processing can be selected from gasification, pyrolysis, reforming, and partial oxidation. In addition, in such embodiments, the carbohydrate source for the homoacetogenic fermentation can be derived from a portion of the carbon-containing material. Also, the step of reducing can be selected from hydrogenation, hydrogenolysis, and reduction by carbon monoxide.

The homoacetogenic fermentation of methods of the present invention can include culturing a microorganism of the genus *Moorella* or *Clostridium* in a fermentation medium. More particularly, the microorganism can be a microorganism of the species *Moorella thermoaceticum* or *Clostridium formicoaceticum*. In other embodiments, the acidogenic fermentation can include culturing a microorganism of the genus *Clostridium* in a medium. More particularly, the acidogenic fermentation can include culturing a microorganism of the species *Clostridium kluyveri* in the medium.

In various embodiments of the invention, the carbohydrate source can be derived from a material having carbon-containing compounds that includes carbohydrate substances and non-carbohydrate substances. The carbohydrate source can be derived from a material comprising containing carbon-containing compounds by fractionating the material to form a carbohydrate-containing fraction for homoacetogenic fermentation and to form a residue fraction comprising lignin for conversion to a product by a thermochemical conversion process. In this embodiment, the product of the thermochemical conversion process can be used in the step of chemically converting a portion of the acetate, acetic acid, or mixtures thereof to ethanol or the step of chemically converting the butyrate, butyric acid, caproate, caproic acid or mixtures thereof to the butanol and hexanol or both. The step of fractionating can be selected from physical treatment, metal ion treatment, ultraviolet light treatment, ozone treatment, oxygen treatment, organosolv treatment, steam explosion treatment, lime impregnation with steam explosion treatment, lime impregnation without steam treatment, hydrogen peroxide treatment, hydrogen peroxide/ozone (peroxone) treatment, acid treatment, dilute acid treatment, or base treatment. Alternatively, the material from which the carbohydrate source is derived can include biomass or can be selected from herbaceous matter, agricultural residue, forestry residue, municipal solid waste, waste paper, pulp and paper mill residue. Further, the material can be selected from trees, shrubs, grasses, wheat, wheat straw, wheat midlings, sugar cane bagasse, corn, corn husks, corn kernel, corn fiber, municipal solid waste, waste paper, yard waste, branches, bushes, energy crops, fruits, fruit peels, flowers, grains, herbaceous crops, leaves, bark, needles, logs, roots, saplings, short rotation woody crops, switch grasses, vegetables, vines, sugar beet pulp, oat hulls, hard woods, wood chips, intermediate streams from pulping operations or soft woods. The material can also be selected from trees, grasses, whole plants, and structural components of plants.

Another method of the present invention produces butanol and hexanol. This method includes conducting an acidogenic fermentation in a medium that includes ethanol and acetate, acetic acid or mixtures thereof. This acidogenic fermentation produces butyrate, butyric acid, caproate, caproic acid or mixtures thereof. The method further includes chemically converting the butyrate, butyric acid, caproate, caproic acid or mixtures thereof to butanol and hexanol. In certain embodiments, the acetate, acetic acid or mixtures thereof is produced by conducting a homoacetogenic fermentation in a medium that includes a carbohydrate source. In addition, the ethanol can be produced by conducting a homoacetogenic fermentation in a medium with a carbohydrate source to produce acetate, acetic acid or mixtures thereof and chemically converting a portion of the acetate, acetic acid or mixtures thereof to ethanol.

In various embodiments of this invention, at least about 70%, at least about 80%, or at least about 90% of the carbon in the ethanol and acetate, acetic acid or mixtures thereof is converted into butanol and hexanol. In other embodiments, essentially none of the carbon in the ethanol and acetate, acetic acid or mixtures thereof is evolved as carbon dioxide. In other embodiments, when the acetate, acetic acid or mixtures thereof is produced by a homoacetogenic fermentation in a medium comprising a carbohydrate source, and the carbohydrate source is a material comprising carbon-containing compounds with less than about 75% by weight of the carbon-containing compounds being carbohydrate substances, the chemical energy efficiency of the method can be at least about 50%, at least about 60%, or at least about 70%. Alternatively, when the acetate, acetic acid or mixtures thereof is produced by a homoacetogenic fermentation in a medium with carbohydrate source, and the carbohydrate source is a material that includes carbon-containing compounds with less than about 75% by weight of the carbon-containing compounds being carbohydrate substances, the yield of butanol and hexanol can be at least about 100 gal/BDT of carbohydrate source, at least about 120 gal/BDT of carbohydrate source, or at least about 140 gal/BDT of carbohydrate source.

In this method, the steps of chemically converting a portion of the acetate, acetic acid or mixtures thereof to ethanol and of chemically converting butyrate, butyric acid, caproate, caproic acid or mixtures thereof to butanol and hexanol can include the specific chemical converting process steps described above. Further, in this method, the microorganisms for conducting either a homoacetogenic fermentation or an acidogenic fermentation can be the same as specifically described above. Further, in this method, the carbohydrate source can be the same as specifically described above.

Another method of the present invention is a method to produce butanol and hexanol from a material having carbon-containing compounds that includes carbohydrate substances and non-carbohydrate substances. This method includes conducting a homoacetogenic fermentation in a medium that includes at least a portion of the carbohydrate substances to produce acetate, acetic acid or mixtures thereof. At least a portion of the non-carbohydrate substances are processed by a thermochemical processing method to produce a reductant. A portion of the acetate, acetic acid or mixtures thereof is chemically converted to ethanol using the reductant. The method further includes conducting an acidogenic fermentation in a medium that includes the ethanol and a portion of the acetate, acetic acid or mixtures thereof to produce butyrate, butyric acid, caproate, caproic acid or mixtures thereof, which are chemically converted to the butanol and hexanol using the reductant.

In this method, the step of chemically converting the acetate, acetic acid or mixtures thereof to ethanol can include acidifying the homoacetogenic fermentation medium to convert acetate to acetic acid, esterifying the acetic acid, and reducing the acetic acid ester to form ethanol using the reductant. This embodiment also includes the step of chemically converting butyrate, butyric acid, caproate, caproic acid or mixtures thereof to butanol and hexanol by acidifying the acidogenic fermentation medium to convert butyrate and caproate to butyric acid and caproic acid, esterifying the butyric acid and caproic acid, and reducing the butyric acid and caproic acid esters to form butanol and ethanol using the reductant.

The steps of reducing can be selected from hydrogenation, hydrogenolysis, and reduction by carbon monoxide. The thermochemical processing can be selected from gasification, pyrolysis, reforming, and partial oxidation.

DETAILED DESCRIPTION OF THE INVENTION

Methods of the present invention are for the production of mixtures of butanol and hexanol with high carbon yield and weight yield as well as high energy efficiency. The methods can generally involve the use of a homoacetogenic fermentation and an acidogenic fermentation in which the carbon and weight yields are very high, substantially without the production of carbon dioxide so that substantially all of the carbon substrates in the fermentations are converted to product. The methods can generally involve using a portion of the product of the homoacetogenic fermentation, namely acetate, acetic acid or mixtures, for chemical conversion to ethanol which is then used as a substrate in the subsequent acidogenic fermentation. In addition, a portion of the product of the homoacetogenic fermentation (acetate, acetic acid or mixtures) is also used as a substrate in the subsequent acidogenic fermentation along with the ethanol. The acidogenic fermentation produces butyrate, butyric acid, caproate, caproic acid or a mixture which are then chemically converted to butanol and hexanol. Since the methods involve the use of a homoacetogenic and an acidogenic fermentation, higher carbon and weight yield and better energy efficiency are achieved than for other known methods for producing butanol and hexanol. In addition, particularly high carbon and weight yield and improved energy efficiencies can be achieved when all of the fractions of a complex raw material such as biomass are used. For example, methods of the present invention can include the use of non-carbohydrate fractions in the various chemical conversion steps to provide significant advantages over alternative processes when using biomass as the feedstock.

One particular embodiment of the present invention is a method to produce butanol and hexanol. This method includes conducting a homoacetogenic fermentation in a medium containing a carbohydrate source. The homoacetogenic fermentation step of the process produces acetate, acetic acid or mixtures thereof as an acetic acid intermediate. The process further includes chemically converting a portion of the acetate, acetic acid, or mixture into ethanol. This embodiment further includes conducting an acidogenic fermentation in a medium that comprises both ethanol that is produced by the chemical conversion of the acetate, acetic acid or mixtures of both and a portion of the acetate, acetic acid, or mixture from the homoacetogenic fermentation that is not chemically converted to ethanol. The acidogenic fermentation produces a variety of products including butyrate, butyric acid, caproate, caproic acid or a mixture of all the products. This embodiment further includes chemically converting the butyrate, butyric acid, caproate, caproic acid or mixtures thereof into butanol and hexanol.

Homoacetogenic Fermentation

Preferred processes for conducting a homoacetogenic fermentation to produce acetate, acetic acid or mixtures thereof as an acetic acid intermediate and chemical conversion of the intermediate to ethanol are described in PCT Publication WO 00/53791 for "Process for Producing Ethanol", which is incorporated herein by reference in its entirety. A homoacetogenic fermentation refers to culturing a homoacetogenic microorganism to produce acetic acid, acetate or mixtures thereof. Homoacetogenic microorganisms are a class of bacteria that utilize a unique biochemical pathway to produce acetic acid from sugars with 100% carbon yield. For example, three moles of glucose can be converted to nine moles of acetic acid by *Clostridium thermoaceticum*, as shown below:

$$3C_6H_{12}O_6 \rightarrow 9CH_3COOH \qquad (1)$$

Glucose (or glucose plus xylose) fermentation to acetate by homofermentative acetogen Homoacetogens (or homofermentative microorganisms) internally convert $CO_2$ into acetate. They do not convert any of the carbohydrate to $CO_2$ and only produce acetic acid. Examples of homoactogens are disclosed in Drake, H. L. (editor), Acetogenesis, Chapman & Hall, 1994, which is incorporated herein by reference in its entirety. In addition these homofermentative organisms typically convert a wide range of sugars into acetic acid, including glucose, xylose, fructose, lactose, and others. Thus, they are particularly suited to the fermentation of complex hydrolyzates from biomass.

Suitable microorganisms for conducting a homoacetogenic fermentation include microorganisms of the genera *Moorella* and *Clostridium*. Specifically, microorganisms of the species *Moorella thermoaceticum* (formerly classified as *Clostridium thermoaceticum*) or *Clostridium formicoaceticum* are suitable for conducting a homoacetogenic fermentation of the present invention. There are now about one hundred acetogens known in twenty-two genera, with the most studied by far being *Moorella thermoacetica* (formerly *Clostridium thermoaceticum*). A current review of acetogens can be found in Drake, et al, Ann. NY Acad. Sci. 1125: 100-128 (2008), which is incorporated herein by reference in its entirety.

There are many fermentation media comprising a carbohydrate source suitable for homoacetogenic fermentations of the present invention which are well known in the art. Any suitable media preparation process may be used for the purposes of this invention. In its most general embodiment the current invention does not depend upon a specific carbohydrate source in a fermentation media, but any suitable source may be used. For example, methods for preparation of suitable fermentation media for a homoacetogenic fermentation are described in more detail within WO 00/53791 in the section entitled "Preparation of Suitable Fermentation Substrate" starting at page 10, line 28. As an illustrative example, WO 00/53791 describes the use of corn as a raw material for a fermentation substrate, where several pretreatment steps are performed in corn milling, and subsequent processing is conducted for the use of starch, cellulose, hemicellulose, or protein fractions. Use of corn fractions as a fermentation substrate can be accomplished by overlapping the saccharification activity with the fermentation process in a design called Simultaneous Saccharification and Fermentation (SSF).

In other embodiments, a carbohydrate source in a fermentation medium for the homoacetogenic fermentation can be derived from a material comprising carbon-containing compounds that comprise carbohydrate substances and non-carbohydrate substances, and such a material can be biomass. For example, the biomass can be selected from herbaceous matter, agricultural residue, forestry residue, municipal solid waste, waste paper, pulp or paper mill residue. Alternatively, the material can be selected from trees, shrubs, grasses, wheat, wheat straw, wheat midlings, sugar cane bagasse, corn, corn husks, corn kernel, corn fiber, municipal solid waste, waste paper, yard waste, branches, bushes, energy crops, fruits, fruit peels, flowers, grains, herbaceous crops, leaves, bark, needles, logs, roots, saplings, short rotation woody crops, switch grasses, vegetables, vines, sugar beet pulp, oat hulls, hard woods, wood chips, intermediate streams from pulping operations or soft woods. In addition, the material can be selected from trees, grasses, whole plants, or structural components of plants. In certain embodiments of the present invention, the products are produced from a material comprising carbon-containing compounds, wherein less than about 75% by weight of the carbon-containing compounds are carbohydrate substances. The processes of the present invention are particularly suitable for such materials because the non-carbohydrate substances can be used to produce product in part, such as the use of hydrogen from the gasification of a non-carbohydrate substance in a hydrogenation or hydrogenolysis step.

In some embodiments, the carbohydrate source is derived from a material comprising carbon-containing compounds by fractionating the material to form a carbohydrate-containing fraction for homoacetogenic fermentation, and to form a residue fraction comprising lignin for conversion to a product by a thermochemical conversion process. In such embodiments, the step of fractionating can be selected from physical treatment, metal ion treatment, ultraviolet light treatment, ozone treatment, oxygen treatment, organosolv treatment, steam explosion treatment, lime impregnation with steam explosion treatment, lime impregnation without steam treatment, hydrogen peroxide treatment, hydrogen peroxide/ozone (peroxone) treatment, acid treatment, dilute acid treatment, and base treatment. As described below, the product of the thermochemical conversion process can be used in the step of chemically converting a portion of the acetate, acetic acid or mixtures thereof to ethanol or the step of chemically converting the butyrate, butyric acid, caproate, caproic acid or mixtures thereof to the butanol and hexanol or both.

Process conditions, media and equipment suitable for homoacetogenic fermentation of microorganisms of the present invention are known in the art and can be selected based on the microorganism being used.

The product of the homoacetogenic fermentation step of the process is an acetic acid intermediate that comprises acetate, acetic acid or mixtures thereof. The process further includes chemically converting a portion of the acetate, acetic acid, or mixture into ethanol as described below. In addition, a different portion of the acetate, acetic acid, or mixture, along with the ethanol, is used as a substrate for an acidogenic fermentation, as described below.

Chemical Conversion of Acetic Acid to Ethanol

A portion of the acetic acid intermediate that comprises acetate, acetic acid or mixtures thereof produced by the homoacetogenic fermentation is chemically converted to ethanol. The amount of the acetic acid intermediate that is chemically converted to ethanol depends on the relative amounts of ethanol and acetic acid intermediate required by a microorganism in a subsequent acidogenic fermentation. Preferably, the amount of acetic acid intermediate that is converted to ethanol results in sufficient ethanol that, in combination with the remaining acetic acid intermediate, the needs of the microorganism in a subsequent acidogenic fermentation are met without significant excess of either ethanol or acetic acid intermediate.

A step in the process of chemical conversion can be formation of an ester of acetic acid. Esterification is easy when an organic acid is present in its protonated acid form (e.g. acetic acid) but is more difficult when the organic acid is in a salt form (e.g. calcium acetate). Acetic acid is a weak organic acid with pKa=4.76. If the homoacetogenic fermentation is conducted at near neutral pH (i.e. pH=7.0), the product of the fermentation will largely be an acetate salt rather than the acid. It is possible to directly add a mineral acid, such as sulfuric acid, to a fermentation medium to convert the acetate salt to its protonated form, but this results in the stoichiometric production of a salt coproduct such as gypsum. Massive production of low valued salt coproducts is undesirable for commodity scale production processes. Thus, the acetate salt is preferably converted to the acid, and the acid must be removed from the dilute solution in water.

In one embodiment, the step of acidifying can include introducing carbon dioxide or an acid with a lower pKa than the carboxylic acid being acidified to a solution comprising the salt of the carboxylic acid. In another embodiment, the step of acidifying includes introducing a tertiary amine with carbon dioxide to form an acid/amine complex. For example, carbon dioxide and tributyl amine (TBA) react with calcium acetate to form an amine complex and calcium carbonate:

Acidification: $Ca(Ac)_2 + H_2O + CO_2 + 2TBA \rightarrow 2TBA:HAc + CaCO_3$ (2)

Carbon dioxide is the acidifying agent in the above reaction. When dissolved in water, a weakly acidic solution of carbonic acid is formed. The carbonic acid in turn acidifies the acetate salt, which in turn is converted into the amine complex (i.e. TBA:HAc). Any low pressure source of carbon dioxide (e.g. boiler exhaust gases, lime plant exhausts, $CO_2$ rich off-gases from $H_2$ production, etc.) can be used. Tributyl amine normally forms a separate liquid phase when mixed with water. However, the TBA:HAc complex is water soluble. So when the acidification reaction occurs, the second liquid phase containing TBA disappears and the resulting reaction mixture is a single liquid phase with the calcium carbonate precipitate. Calcium carbonate is essentially insoluble in water, so it can be recovered at nearly 100% yield and recycled for use as a base in fermentation.

This process can further include contacting the acid/amine complex with a water immiscible solvent (e.g., an alcohol capable of forming a separate liquid phase with water (e.g. n-butanol, pentanol, hexanol, octanol, etc.) to form an ester of the water immiscible solvent and the carboxylic acid. The organic extract containing the alcohol and the TBA:HAc complex can be heated and the ester formed directly from the complex:

Esterification: $TBA:HAc + BuOH \rightarrow TBA + BuAc + H_2O$ (3)

Water can be distilled from the reaction mass to drive the reaction to completion. After the reaction is complete, the mixture can be distilled to recover the TBA and excess butanol for recycle, and the butyl acetate intermediate can be further processed. Other water immiscible alcohols can be used including pentanol, hexanol, etc.

Methods of acidification and esterification are described in more detail in PCT Publication WO 2005/073161 for "Energy Efficient Methods to Produce Products" and in WO 2000/53791, both of which are incorporated herein by reference in their entirety.

When an ester is formed in the process of chemical conversion of the acetic acid intermediate to ethanol, the ester can be reduced to form ethanol. For example, the ester can be reduced by a process selected from hydrogenation, hydrogenolysis or reduction by carbon monoxide. Hydrogenolysis refers to simultaneous hydrolysis and hydrogenation. An example of reduction by carbon monoxide is U.S. Pat. No. 4,851,344 for "Microbial Reduction of Monocarboxylic and Dicarboxylic Acids in the Presence of Carbon Monoxide and/or Formates Plus Mediators".

The hydrogenation of esters to produce alcohols is a well-known reaction. U.S. Pat. Nos. 2,782,243, 4,113,662, 4,454, 358, and 4,497,967, which are incorporated herein by reference in their entirety, disclose processes for the hydrogenation of esters of acetic acid to ethanol. Hydrogenation can be performed in either the liquid phase or the gas phase. Any suitable hydrogenation process can be used. This reaction is also an equilibrium reaction. The reaction can be driven to the right by using high partial pressures of hydrogen. Typical reaction conditions are 150° C.-250° C. and 500 psi-3000 psi depending upon the desired conversion and selectivity. The reaction can be catalyzed by any suitable hydrogenation catalysts, such as copper chromite, nickel, Raney nickel, ruthenium, and platinum. A copper chromite, nickel, or Raney nickel catalyst is preferred for the hydrogenation since these catalysts are not poisoned by water. In the liquid phase process, an alcohol such as ethanol is a good solvent.

As an example of hydrogenolysis, in a gas phase process, an ester feed can be vaporized and fed to a hydrogenation reactor with an excess of hydrogen. After passing through the bed, the vapors are cooled and flashed into a low pressure knockout drum. The hydrogen rich vapor phase is recycled back to the reactor. The product (e.g., ethanol) is separated from unreacted ester and alcohol solvent which can be recycled for further reaction.

Another refining process such as a distillation column can be used as a final polishing step, depending upon the nature and quantities of side products from the esterification and hydrogenation units.

Preferred acetate esters for the production of ethanol are butyl acetate or hexyl acetate, as each avoids the introduction of a second compound into the process which must be purified away from the product stream.

A water stripper can be used to collect water streams from the acidification, esterification, and hydrogenation units. The water can be steam stripped to recover solvent values, then the water is sent to final treatment and discharge or recycled to the fermentation section.

Many potential sources of hydrogen for use in the present invention exist. Any suitable hydrogen source can be used that produces hydrogen of sufficient purity for the hydrogenation reaction and that will not poison the catalyst. Raw materials for hydrogen production include water from which hydrogen can be produced by electrolysis. Many fossil and renewable organic feedstocks can also be used. If a fossil feedstock is used, such as methane from natural gas, some $CO_2$ will be produced along with the hydrogen. However, if a renewable feedstock is used then the $CO_2$ production will be neutral to the environment. For example, almost any feedstock that contains carbon can be used to produce hydrogen. Wood chips, sawdust, municipal wastes, recycled paper, wastes from the pulp and paper industry, solid agricultural wastes from animal and/or crop production are all examples of renewable feedstocks that can be used for hydrogen production, e.g., using gasification technology.

Steam reforming of methane to produce hydrogen is a well know process. Natural gas and water can be reacted in a steam reformer to form hydrogen and carbon dioxide. Other methods to produce hydrogen (partial oxidation of hydrocarbons, partial oxidation of coal, water electrolysis, etc.) could also be used. Where pure oxygen is available, such as in a fenceline operation with an air separations plant, the partial oxidation processes can be economically viable. Where inexpensive sources of electricity are available, electrolysis can be viable.

In a preferred embodiment, hydrogen can be obtained from a material comprising carbon-containing compounds that comprises carbohydrate substances and non-carbohydrate substances as described in WO 2008/098254 for "Energy Efficient Methods to Produce Products" which is incorporated herein by reference in its entirety. As described in detail in WO 2008/098254, thermochemical conversion processes can be used to convert non-carbohydrate substances. Such thermochemical conversion processes can include gasification, pyrolysis, reforming, and partial oxidation. Such processes can produce intermediates that can include hydrogen, carbon monoxide, carbon dioxide, methanol and/or mixtures thereof. An important part of this embodiment is that it provides the ability to use all of the fractions of a complex raw material such as biomass because while a carbohydrate fraction of a complex raw material is converted by the fermentation step, the non-carbohydrate residue of the complex raw material can be converted to hydrogen for the chemical conversion step. This is a key factor in the advantage of this embodiment over alternative processes when using biomass as the feedstock.

Acidogenic Fermentation

Methods of the present invention can further include conducting an acidogenic fermentation in a medium comprising the ethanol and a portion of the acetate, acetic acid or mixtures thereof to produce butyrate, butyric acid, caproate, caproic acid or mixtures thereof. The term, acidogenic, as used herein refers to a fermentation process that converts a carbon source to one or more organic acids, without the production of carbon dioxide. Such a process can include the production of other species, such as hydrogen.

Acidogenic fermentations can be conducted by culturing microorganisms that convert a carbon source to one or more organic acids, without the production of carbon dioxide. For example, species of the bacteria *Clostridium* can convert ethanol and acetic acid to butanol and caproic acid. Particularly, *Clostridium kluyveri* can convert ethanol and acetic acid essentially to butyric acid, caproic acid and hydrogen in a process under which no $CO_2$ is produced (see, e.g., Stanier et al, *Microbial World*, Prentice Hall, 1976; Thauer et al., European J. Biochem., 4 (1968) pp. 173-180, both of which are hereby incorporated by reference in their entirety). A strain of *Clostridium kluyveri* is available from the ATCC as ATCC 8527.

(4)

Fermentation of ethanol and acetic acid to butyric acid and caproic acid

Process conditions, media and equipment suitable for fermentation of microorganisms of the present inventions are known in the art and can be selected based on the microorganism being used.

Chemical Conversion of Butyric Acid and Caproic Acid to Butanol and Hexanol

The steps of acidification, esterification and reduction described above for chemical conversion of acetic acid to ethanol can be used for chemically converting the butyrate, butyric acid, caproate, caproic acid or mixtures thereof to the butanol and hexanol.

(5)

Conversion of butyric acid and caproic acid to butanol and hexanol by esterification and hydrogenolysis.

The theoretical yield of this route for the production of alcohols from carbohydrates is 63% w/w, which is more than about 50% higher than the alternative processes previously disclosed (32% w/w for the ABE process and 41% w/w for the process of US Patent Publication 2008/0248540).

Various embodiments of the present invention are highly efficient at converting carbon in a carbohydrate source to butanol and hexanol. More particularly, in preferred embodiments of the present invention, at least about 70% of carbon in the carbohydrate source is converted into the butanol and hexanol, at least about 75% of carbon in the carbohydrate source is converted into the butanol and hexanol, at least about 80% of carbon in the carbohydrate source is converted into the butanol and hexanol, at least about 85% of carbon in the carbohydrate source is converted into the butanol and hexanol, at least about 90% of carbon in the carbohydrate source is converted into the butanol and hexanol, or at least about 95% of carbon in the carbohydrate source is converted into the butanol and hexanol. In other embodiments, essentially none of the carbon in the carbohydrate source is evolved as carbon dioxide.

The chemical energy efficiency of methods of the present invention for producing butanol and hexanol can be very high. For example, the chemical energy efficiency of such methods for producing butanol and hexanol from a material comprising carbon-containing compounds, wherein less than about 75% by weight of the carbon-containing compounds are carbohydrate substances can be at least about 50%, at least about 55%, at least about 60%, at least about 65%, at least about 70%, at least about 75%.

The present invention can also achieve high yields of butanol and hexanol. Specifically, the yield of butanol and hexanol when being produced from a material comprising carbon-containing compounds, wherein less than about 75% by weight of the carbon-containing compounds are carbohydrate substances can be at least about 100 gal/BDT of carbohydrate source, be at least about 110 gal/BDT of carbohydrate source, be at least about 120 gal/BDT of carbohydrate source, be at least about 130 gal/BDT of carbohydrate source, be at least about 140 gal/BDT of carbohydrate source, be at least about 150 gal/BDT of carbohydrate source.

A particular embodiment of the present invention is a method to produce butanol and hexanol from a material comprising carbon-containing compounds that comprise carbohydrate substances and non-carbohydrate substances. The method includes conducting a homoacetogenic fermentation in a medium comprising at least a portion of the carbohydrate substances to produce acetate, acetic acid or mixtures thereof. The method further includes processing at least a portion of the non-carbohydrate substances by thermochemical processing to produce a reductant and chemically converting a portion of the acetate, acetic acid or mixtures thereof to ethanol using the reductant. An acidogenic fermentation is conducted in a medium comprising the ethanol and a portion of the acetate, acetic acid or mixtures thereof to produce butyrate, butyric acid, caproate, caproic acid or mixtures thereof. The method then includes chemically converting the butyrate, butyric acid, caproate, caproic acid or mixtures thereof to the butanol and hexanol using the reductant. In some embodiments, the step of chemically converting a portion of the acetate, acetic acid or mixtures thereof to ethanol comprises acidifying the homoacetogenic fermentation medium to convert acetate to acetic acid; esterifying the acetic acid; and reducing the acetic acid ester to form ethanol using the reductant. Those embodiments also include the step of chemically converting butyrate, butyric acid, caproate, caproic acid or mixtures to butanol and hexanol comprises acidifying the acidogenic fermentation medium to convert butyrate and caproate to butyric acid and caproic acid; esterifying the butyric acid and caproic acid; and reducing the butyric acid and caproic acid esters to form butanol and ethanol using the reductant. In these embodiments, the steps of reducing can be selected from hydrogenation, hydrogenolysis and reduction by carbon monoxide. In addition, the thermochemical processing can be selected from gasification, pyrolysis, reforming, and partial oxidation.

A further embodiment of the present invention is a method to produce butanol and hexanol that includes conducting an acidogenic fermentation. The fermentation is conducted in a medium that includes ethanol and acetate, acetic acid or mixtures thereof. The fermentation produces butyrate, butyric acid, caproate, caproic acid or mixtures thereof. The method further includes chemically converting the butyrate, butyric acid, caproate, caproic acid or mixtures thereof to the butanol and hexanol. In this embodiment, the ethanol and the acetate, acetic acid or mixtures thereof can be derived from any source. For example, the ethanol can be produced by any conventional ethanol production method, such as yeast fermentation of glucose from corn dry milling or wet milling or yeast fermentation from cane sugar juice or molasses. The acetate, acetic acid or mixtures thereof can also be produced by any conventional production method, such as the petrochemical route from natural gas, or the vinegar process from ethanol. However, in some embodiments, the acetate, acetic acid or mixtures thereof are produced by conducting a homoacetogenic fermentation in a medium that includes a carbohydrate source to produce acetate, acetic acid or mixtures thereof. In still other embodiments, the ethanol is produced by conducting a homoacetogenic fermentation in a medium that includes a carbohydrate source to produce acetate, acetic acid or mixtures thereof a portion of which is then chemically converted to ethanol.

This method of converting ethanol and acetate, acetic acid or mixtures thereof to butanol and hexanol is highly efficient at converting carbon in a carbohydrate source to butanol and hexanol because of the use of an acidogenic fermentation. More particularly, in preferred embodiments of the method, at least about 70% of carbon in the carbon source (i.e., ethanol and acetate, acetic acid or mixtures thereof) is converted into the butanol and hexanol, at least about 75% of carbon source is converted into the butanol and hexanol, at least about 80% of carbon source is converted into the butanol and hexanol, at least about 85% of carbon source is converted into the butanol and hexanol, at least about 90% of carbon source is converted into the butanol and hexanol, or at least about 95% of carbon source is converted into the butanol and hexanol. In other embodiments, essentially none of the carbon in the ethanol and acetate, acetic acid or mixtures thereof is evolved as carbon dioxide.

Figure 1:
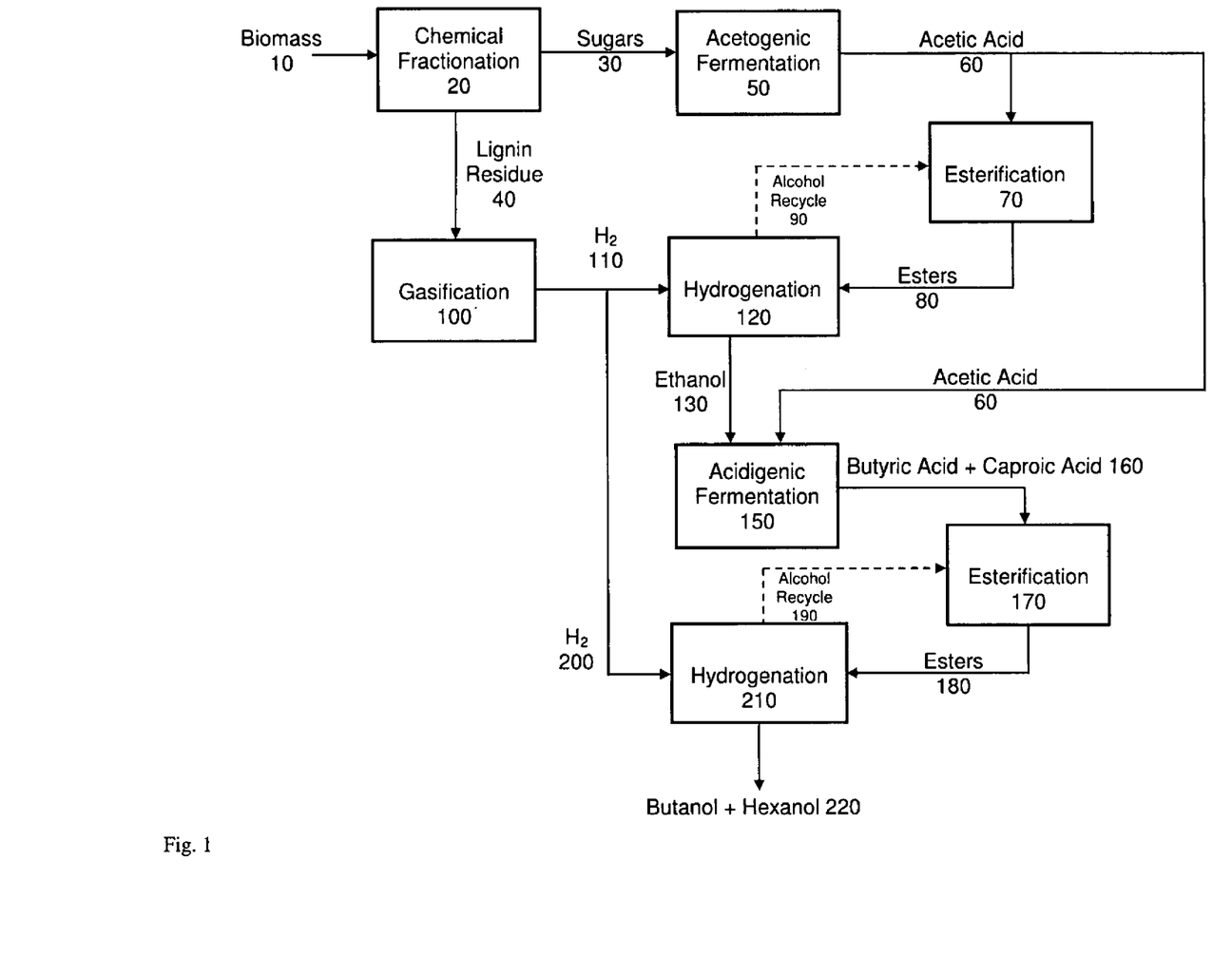
FIG. 1 illustrates a specific embodiment of the invention for the production of butanol and hexanol having an acetogenic and an acidogenic fermentation.

With reference to FIG. 1, a specific embodiment of the present invention is illustrated wherein a biomass feedstock comprising approximately 60% carbohydrate and 40% residue, which is typical of most biomass such as wood or grasses is converted to butanol and hexanol. A biomass 10 is subjected to chemical fractionation 20. The biomass 10 can be selected from a wide range of materials as is generally described above. One fraction 30 comprises fermentable sugars or materials that can readily be converted to fermentable sugars. For example, biomass typically includes a carbohydrate fraction and a non-carbohydrate fraction. The carbohydrate fraction can include cellulose, hemicellulose, starch and sugars. Cellulose, hemicellulose and starch typically include sugars such as glucose, xylose, arabinose, mannose, etc. Another fraction 40 is a non-carbohydrate fraction that can include lignin, which is a complex phenolic material, as well as proteins, resinous materials and minerals. The fraction 40 can be put through a gasification process 100 where hydrogen gas 110 is produced. The hydrogen gas 110 may either be used in the step of hydrogenation 120 for the purpose of producing ethanol 130, or be utilized in the hydrogenation 210 step to produce butanol and hexanol 220.

The fraction 30 that comprises fermentable sugars or materials that can readily be converted to fermentable sugars is used as a substrate in an acetogenic fermentation 50. The product of the acetogenic fermentation 50 is acetate, acetic acid and mixtures thereof and the fermentation medium comprising these components can be acidified to acetic acid 60. The purpose of the fermentation process is to convert fermentable carbohydrates into acetic acid. The acetic acid 60 is then directed through an esterification process 70 with an alcohol 90, such as methyl or ethyl alcohol, to form volatile esters 80. A reactive distillation process can be used to drive the acidification and esterification processes to a high conversion. The conversion of the ester 80 of the acetic acid 60 into two alcohols is achieved by hydrogenation 120 using hydrogen 110 from the gasification process 100. Many potential sources of hydrogen exist for this process, but any source that produces hydrogen of sufficient purity for the reaction and will not poison a hydrogenation catalyst may be used. The hydrogenation process 120 forms ethanol 130 and another alcohol 90. The other alcohol 90 is recycled back to the step of esterification. The other alcohol 90 can be any alcohol, including ethanol.

Fractions of ethanol 130 from hydrogenation 120 and acetic acid 60 from the acetogenic fermentation 50 are combined for use as a substrate in an acidogenic fermentation 150 to produce butyric acid, butyrate, caproic acid, caproate and mixtures thereof and the fermentation medium comprising these components can be acidified to butyric acid and caproic acid 160. The butyric and caproic acids 160 are subjected to an esterification process 170 where the acids are converted into esters 180. The conversion of the ester 180 of the butyric and caproic acids 160 into alcohols is achieved by hydrogenation 210. Hydrogen gas 200 from the gasification process 100 is supplied to the hydrogenation step 210. The hydrogenation 210 of the esters 180 of butyric and caproic acids 160 converts the esters into butanol, hexanol, and mixtures thereof 220 and another alcohol 190. The other alcohol 190 produced by the hydrogenation process 210 is recycled 190 back to the esterification step 170 of the acid mixture.

Figure 2:
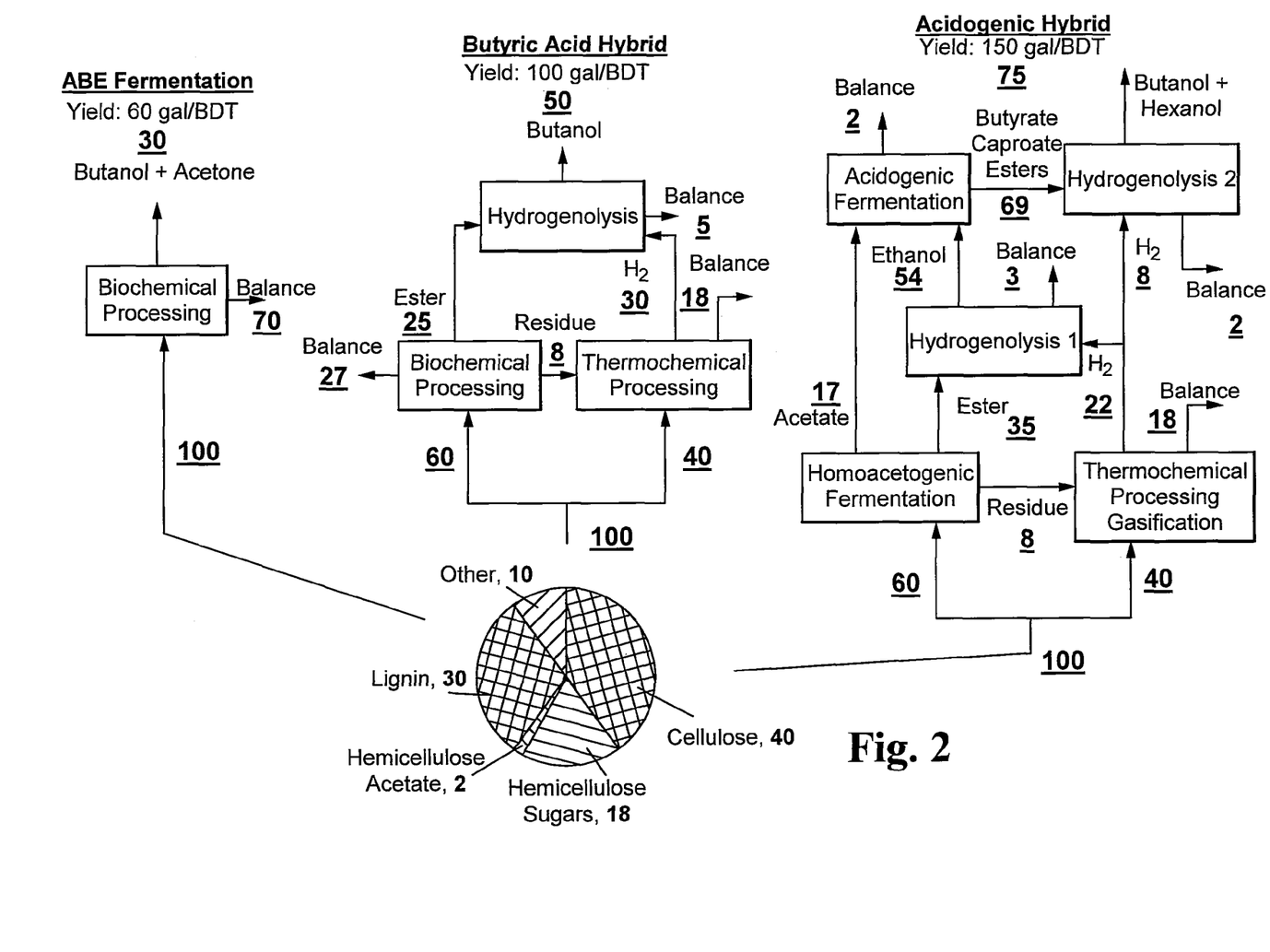
FIG. 2 is a comparison of the chemical energy flows and chemical efficiencies of an ABE fermentation process, a butyric acid hybrid process and a process of the invention when using biomass such as wood as the raw material.

Processes of the present invention provide significantly higher capture of chemical energy flows from biomass to higher alcohol product and higher chemical efficiencies than other known technologies. With reference to FIG. 2, a comparison between two known technologies for producing butanol and an embodiment of the present invention are shown. The different paths in FIG. 2 show the various process steps in the three different technologies, along with the chemical energy flows, normalized to the starting biomass being equal to 100, shown in bolded and underlined numbers. Also shown is the chemical efficiency for each of the technologies, with a yield of 200 gal/BDT (Bone Dry Ton) assumed to be 100% chemical efficiency based on the energy content (HHV-higher heating value) of wood.

The ABE Fermentation technology calculations are based on *Acetone-Butanol Fermentation Revisited*, Microbial Reviews, December 2006; 50(4); 484-524, and the Butyric Acid Hybrid technology calculations are based on US Patent Publication 2008/0248540. The Acidogenic Hybrid technology is an embodiment of the present invention. As shown in FIG. 2, the chemical energy flow for the ABE Technology results in 30% of the chemical energy of the starting biomass being converted to butanol, ethanol and acetone and the Butyric Acid Hybrid technology results in 50% of the chemical energy of the starting biomass being converted to butanol. In contrast, the Acidogenic Hybrid technology of the present invention results in 75% of the chemical energy of the starting biomass being converted to butanol and hexanol. In addition, the yield for the Acidogenic Hybrid technology of the present invention is 150 gal/BDT, which is significantly higher than the yields of the Butyric Acid Hybrid technology (100 gal/BDT) and the ABE Technology (60 gal/BDT).

While various embodiments of the present invention have been described in detail, it is apparent that modifications and adaptations of those embodiments will occur to those skilled in the art. However, it is to be expressly understood that such modifications and adaptations are within the spirit and scope of the present invention.

What is claimed is:

1. A method to produce butanol and hexanol, comprising:
    (a) culturing a homoacetogenic microorganism in a fermentation medium comprising a carbohydrate source to produce acetate, acetic acid or mixtures thereof;
    (b) chemically converting a portion of the acetate, acetic acid or mixtures thereof to ethanol;
    (c) culturing an acidogenic microorganism in a fermentation medium comprising the ethanol and a portion of the acetate, acetic acid or mixtures thereof to produce a first intermediate selected from the group consisting of butyrate, butyric acid, and mixtures thereof, and a second intermediate selected from the group consisting of caproate, caproic acid, and mixtures thereof; and
    (d) chemically converting the first intermediate into butanol and the second intermediate into hexanol.

2. The method of claim 1, wherein at least about 70% of carbon in the carbohydrate source is converted into the butanol and hexanol.

3. The method of claim 1, wherein at least about 80% of carbon in the carbohydrate source is converted into the butanol and hexanol.

4. The method of claim 1, wherein at least about 90% of carbon in the carbohydrate source is converted into the butanol and hexanol.

5. The method of claim 1, wherein essentially none of the carbon in the carbohydrate source is evolved as carbon dioxide.

6. The method of claim 1, wherein the step of chemically converting a portion of the acetate, acetic acid or mixtures thereof to ethanol comprises acidifying the homoacetogenic fermentation medium to convert acetate to acetic acid; esterifying the acetic acid; and reducing the acetic acid ester to form ethanol.

7. The method of claim 6, wherein the step of acidifying comprises introducing carbon dioxide or an acid with a lower pKa than acetic acid to the fermentation medium comprising a salt of acetic acid.

8. The method of claim 6, wherein said step of acidifying comprises introducing an amine with carbon dioxide to the fermentation medium to form an acetic acid/amine complex.

9. The method of claim 8, further comprising contacting the acid/amine complex with a water immiscible solvent to form an ester of the water immiscible solvent and the acetic acid.

10. The method of claim 1, wherein the step of chemically converting the first intermediate into butanol and the second intermediate into hexanol comprises acidifying the acidogenic fermentation medium to convert butyrate and caproate to butyric acid and caproic acid; esterifying the butyric acid and caproic acid; and reducing the butyric acid and caproic acid esters to form butanol and ethanol.

11. The method of claim 10, wherein the step of acidifying comprises introducing carbon dioxide or an acid with a lower pKa than butyric acid and caproic acid to the fermentation medium comprising a salt of butyric acid and caproic acid.

12. The method of claim 10, wherein said step of acidifying comprises introducing an amine with carbon dioxide to the fermentation medium to form butyric acid/amine and caproic acid/amine complexes.

13. The method of claim 12, further comprising contacting the acid/amine complexes with a water immiscible solvent to form an ester of the water immiscible solvent and the butyric acid and an ester of the water immiscible solvent and the caproic acid.

14. The method of claim 6 or 10, wherein a reductant for the step of reducing is produced by thermochemical processing of a portion of a carbon-containing material.

15. The method of claim 14, wherein the thermochemical processing is selected from the group consisting of gasification, pyrolysis, reforming, and partial oxidation.

16. The method of claim 14, wherein the carbohydrate source is derived from a portion of the carbon-containing material.

17. The method of claim 6 or 10, wherein the step of reducing is selected from the group consisting of hydrogenation, hydrogenolysis and reduction by carbon monoxide.

18. The method of claim 1, wherein the step of conducting a homoacetogenic microorganism is from the genus *Moorella* or *Clostridium*.

19. The method of claim 1, wherein the homoacetogenic microorganism is *Moorella thermoaceticum* or *Clostridium formicoaceticum*.

20. The method of claim 1, wherein the acidogenic microorganism is from the genus *Clostridium*.

21. The method of claim 1, wherein the acidogenic microorganism *Clostridium kluyveri*.

22. The method of claim 1, wherein the carbohydrate source is derived from a material comprising carbon-containing compounds that comprises carbohydrate substances and non-carbohydrate substances.

23. The method of claim 22, wherein the carbohydrate source is derived from a material comprising carbon-containing compounds by fractionating the material to form a carbohydrate-containing fraction for homoacetogenic fermentation, and to form a residue fraction comprising lignin for conversion to a product by a thermochemical conversion process.

24. The method of claim 23, wherein the product of the thermochemical conversion process is used in the step of chemically converting a portion of the acetate, acetic acid or mixtures thereof to ethanol or the step of chemically converting the first intermediate to the butanol and the second intermediate to the hexanol, or both.

25. The method of claim 23, wherein the step of fractionating is selected from the group consisting of physical treatment, metal ion treatment, ultraviolet light treatment, ozone treatment, oxygen treatment, organosolv treatment, steam explosion treatment, lime impregnation with steam explosion treatment, lime impregnation without steam treatment, hydrogen peroxide treatment, hydrogen peroxide/ozone (peroxone) treatment, acid treatment, dilute acid treatment, and base treatment.

26. The method of claim 22, wherein the material comprises biomass.

27. The method of claim 22, wherein the material is selected from the group consisting of herbaceous matter, agricultural residue, forestry residue, municipal solid waste, waste paper, pulp and paper mill residue.

28. The method of claim 22, wherein the material is selected from the group consisting of trees, shrubs, grasses, wheat, wheat straw, wheat midlings, sugar cane bagasse, corn, corn husks, corn kernel, corn fiber, municipal solid waste, waste paper, yard waste, branches, bushes, energy crops, fruits, fruit peels, flowers, grains, herbaceous crops, leaves, bark, needles, logs, roots, saplings, short rotation woody crops, switch grasses, vegetables, vines, sugar beet pulp, oat hulls, hard woods, wood chips, intermediate streams from pulping operations and soft woods.

29. The method of claim 22, wherein the material is selected from the group consisting of trees, grasses, whole plants, and structural components of plants.

30. The method of claim 1, wherein the carbohydrate source is a material comprising carbon-containing compounds, wherein less than about 75% by weight of the carbon-containing compounds are carbohydrate substances and the chemical energy efficiency of the method is at least about 50%.

31. The method of claim 1, wherein the carbohydrate source is a material comprising carbon-containing compounds, wherein less than about 75% by weight of the carbon-containing compounds are carbohydrate substances and the chemical energy efficiency of the method is at least about 60%.

32. The method of claim 1, wherein the carbohydrate source is a material comprising carbon-containing compounds, wherein less than about 75% by weight of the carbon-containing compounds are carbohydrate substances and the chemical energy efficiency of the method is at least about 70%.

33. The method of claim 1, wherein the carbohydrate source is a material comprising carbon-containing compounds, wherein less than about 75% by weight of the carbon-containing compounds are carbohydrate substances and the yield of butanol and hexanol is at least about 100 gal/BDT of carbohydrate source.

34. The method of claim 1, wherein the carbohydrate source is a material comprising carbon-containing compounds, wherein less than about 75% by weight of the carbon-containing compounds are carbohydrate substances and the yield of butanol and hexanol is at least about 120 gal/BDT of carbohydrate source.

35. The method of claim 1, wherein the carbohydrate source is a material comprising carbon-containing compounds, wherein less than about 75% by weight of the carbon-containing compounds are carbohydrate substances and the yield of butanol and hexanol is at least about 140 gal/BDT of carbohydrate source.

36. A method to produce butanol and hexanol, comprising:
(a) culturing an acidogenic microorganism in a fermentation medium comprising ethanol and acetate, acetic acid or mixtures thereof to produce a first intermediate selected from the group consisting of butyrate, butyric acid, and mixtures thereof, and a second intermediate selected from the group consisting of caproate, caproic acid, and mixtures thereof; and
(b) chemically converting the first intermediate into butanol and the second intermediate into hexanol.

* * * * *

UNITED STATES PATENT AND TRADEMARK OFFICE
CERTIFICATE OF CORRECTION

PATENT NO. : 8,252,567 B2  
APPLICATION NO. : 12/368040  
DATED : August 28, 2012  
INVENTOR(S) : Dan W. Verser Page 1 of 1

It is certified that error appears in the above-identified patent and that said Letters Patent is hereby corrected as shown below:

In column 15, claim 18, lines 23-24, delete "step of conducting a"

Signed and Sealed this
First Day of January, 2013

David J. Kappos
*Director of the United States Patent and Trademark Office*